United States Patent
Mathies

(10) Patent No.: US 8,920,830 B2
(45) Date of Patent: Dec. 30, 2014

(54) TEMPERATURE REDUCING, HEALING WOUND DRESSING

(75) Inventor: Burkhard Mathies, Givrins (CH)

(73) Assignee: Laboratoire Medidom S.A., Sarnen (CH)

( * ) Notice: Subject to any disclaimer, the term of this patent is extended or adjusted under 35 U.S.C. 154(b) by 389 days.

(21) Appl. No.: 13/003,106

(22) PCT Filed: Jul. 7, 2009

(86) PCT No.: PCT/EP2009/058550
§ 371 (c)(1),
(2), (4) Date: Jun. 1, 2011

(87) PCT Pub. No.: WO2010/003935
PCT Pub. Date: Jan. 14, 2010

(65) Prior Publication Data
US 2011/0311610 A1    Dec. 22, 2011

Related U.S. Application Data

(60) Provisional application No. 61/078,447, filed on Jul. 7, 2008.

(51) Int. Cl.
*A61F 13/00* (2006.01)
*A61F 13/02* (2006.01)

(52) U.S. Cl.
CPC ..... *A61F 13/00012* (2013.01); *A61F 13/00029* (2013.01); *A61F 13/00034* (2013.01); *A61F 13/00063* (2013.01); *A61F 13/0209* (2013.01); *A61F 2013/00187* (2013.01); *A61F 2013/00255* (2013.01); *A61F 2013/00604* (2013.01); *A61F 2013/0071* (2013.01); *A61F 2013/00748* (2013.01); *A61F 2013/00863* (2013.01); *A61F 2013/00919* (2013.01); *A61F 2013/00931* (2013.01)

USPC ............... 424/443; 424/445; 424/449; 560/5; 560/51; 560/54; 562/400; 562/403; 602/2; 604/289; 604/304

(58) Field of Classification Search
USPC .......... 424/443, 445, 447, 449; 560/5, 51, 54; 562/400, 403; 602/2; 604/289, 304
See application file for complete search history.

(56) References Cited

U.S. PATENT DOCUMENTS

| 4,668,564 A | 5/1987 | Orchard ...................... 428/246 |
| 5,658,582 A | 8/1997 | Dorigatti et al. |

(Continued)

FOREIGN PATENT DOCUMENTS

| DE | 101 35 676 A1 | 2/2003 |
| JP | 7-16256 A | 6/2013 |
| JP | 2001017531 A | 9/2013 |
| RU | 2249467 C2 | 5/2004 |
| RU | 2004101621 A | 7/2005 |
| RU | 70 792 U1 | 2/2008 |
| WO | WO 2005/067837 A1 | 7/2005 |

OTHER PUBLICATIONS

Jones et al., Wound dressings; Apr. 1, 2006; British Medical Journal; 332(7544):777-780; "Wound dressings", PubMed [online], [retrieved Mar. 24, 2014] Retrieved from the Internet:<URL: http://www.ncbi.nlm.nih.gov/pmc/articles/PMC1420733/>.*

Magnani et al., "Biological performance of two materials based on sulfated hyaluronic acid and polyurethane," *J. Mater. Chem.* 9:2393-2398, 1999.

*Primary Examiner* — Jane C Oswecki
(74) *Attorney, Agent, or Firm* — Seed IP Law Group PLLC

(57) ABSTRACT

The present invention relates to wound dressings having a wound contacting layer that contains a wound healing composition and which is adapted to maintain a temperature different from ambient, for example achieve and maintain a heat-absorbing effect on the underlying tissues. The specific physico-chemical structure of the devices of the invention allows fluid containment and absorption of wound secretions while avoiding skin macerations.

10 Claims, 7 Drawing Sheets

(56) References Cited

U.S. PATENT DOCUMENTS

| | | | |
|---|---|---|---|
| 5,750,585 A | 5/1998 | Park et al. .................... 521/143 |
| 5,759,570 A | 6/1998 | Arnold |
| 6,331,298 B1 | 12/2001 | Ferguson et al. |
| 6,566,575 B1 | 5/2003 | Stickels et al. .................. 602/41 |
| 6,800,278 B1 | 10/2004 | Perrault et al. ............. 424/78.06 |
| 2004/0153040 A1* | 8/2004 | Martineau et al. ............ 604/304 |
| 2005/0080368 A1* | 4/2005 | Hurwitz ............................ 602/2 |
| 2007/0066924 A1 | 3/2007 | Hopman et al. |
| 2007/0088104 A1* | 4/2007 | Hung et al. .................... 524/31 |
| 2008/0058747 A1 | 3/2008 | Singh Kainth et al. |

* cited by examiner

1. Influence of ions

2. Influence of pH

TEMPERATURE REDUCING, HEALING WOUND DRESSING

FIELD OF THE INVENTION

The present invention is in the field of wound covering devices having particular physical surface layer features and which contain compositions designed to promote healing of the wound.

BACKGROUND OF THE INVENTION

Wound covering devices are known in the art. However, there still exists the need for wound dressings that promote wound healing, allow fluid containment and absorption of wound secretions. The present invention meets this need.

SUMMARY OF THE INVENTION

The present invention relates to wound dressings having a wound contacting layer that contains a wound healing composition and which is adapted to maintain a temperature different from ambient, for example achieve and maintain a heat-absorbing effect on the underlying tissues. The specific physico-chemical structure of the devices of the invention allows fluid containment and absorption of wound secretions whilst avoiding skin macerations.

In one aspect, the present invention thus relates to a cold adapted wound dressing device designed to promote healing of a wound to which it is applied, the dressing device comprising:
  a wound covering having a wound contacting layer with a wound contacting surface;
  a wound treatment material contained in the wound contacting layer; and
  a heat absorbing layer in heat flow communication with the wound contacting layer,
wherein the heat absorbing layer is adaptable to remove heat from the wound contacting layer and to reduce a temperature of the wound contacting surface to below an ambient temperature.

In another aspect, the present invention is directed to a method for promoting healing of a wound comprising applying the wound dressing device of the invention to the wound.

BRIEF DESCRIPTION OF THE DRAWINGS

FIG. 10 A shows the agglomerated bead morphology of the thus produced SAPs, whereas FIG. 10B shows the broccoli-like morphology.

DESCRIPTION OF THE INVENTION

The present invention is a cold adapted wound dressing device, which has cooling and liquid absorption capabilities, and is useful in sterile and non-sterile environments for dressing wounds and other injuries. The present invention is not a bandage in the broad usage, because it is adapted to be sterilizable and to be in direct contact with a dermal/transdermal wound or surgical incision on the body. The cooling ability of the device is intended to temporarily lower the temperature of the body at the site of application, and to provide the attendant benefits of such a local temperature reduction.

Figure 5:
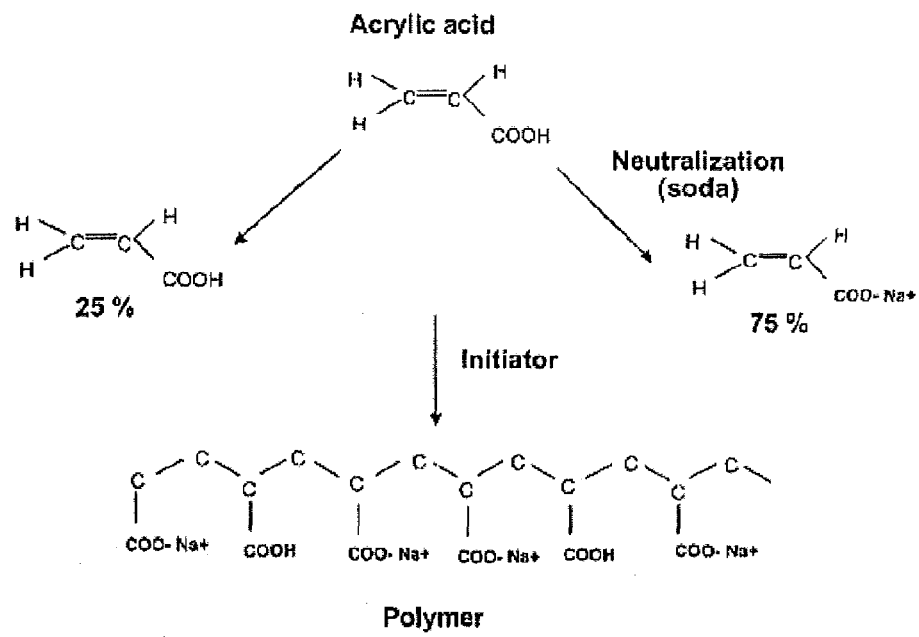
FIG. 5 is a reaction scheme depicting the polymerization of acrylic acid and sodium acrylate.

In a preferred embodiment, a heat-sink made of hydrated absorbent polymers is contained in a portion of the device. Preferably, the hydrated polymers are of a type known as: super-absorbent polymers (SAPs) in the form of a hydrogel. See for examples: U.S. Pat. No. 4,668,564 to Orchard, and U.S. Pat. No. 5,750,585 to Park et al. Super-Absorbent Polymers typically are cross-linked copolymers of acrylic acid and sodium acrylate (FIG. 5). Other materials for super-absorbent polymers comprise, but are not limited to, polyacrylamide copolymer, ethylene maleic anhydride copolymer, cross-linked carboxy-methyl-cellulose, polyvinyl alcohol copolymers, cross-linked polyethylene oxide, and starch grafted copolymer of polyacrylonitrile. They are commercially available in a powder or particulate form. These materials are characterized as super-absorbent in that they are able to rapidly (i.e., in a few seconds under appropriate conditions) adsorb on the order of 500 time their weight in pure water.

Figure 6:
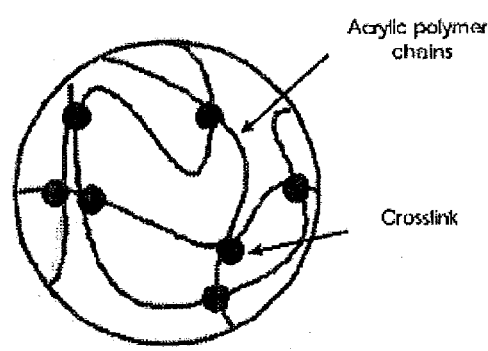
FIG. 6 is a schematic depiction of a cross-linked polymer.

For this material to obtain "super-absorbent" properties, requires cross-linking the copolymer chains with a cross-linking agent, such as a bifunctional molecule. The bifunctional molecule must be able to react with the free carboxylic groups. After cross-linking, the polymer chains are attached to one another (FIG. 6).

Exemplary cross-linking agents comprise, but are not limited to polyhydroxy compounds, diepoxy compounds, isocyanates, ethyleneglycoldimethacrylate (EGDM), and N,N-methylenebisacrylamide (BIS).

Figure 7:
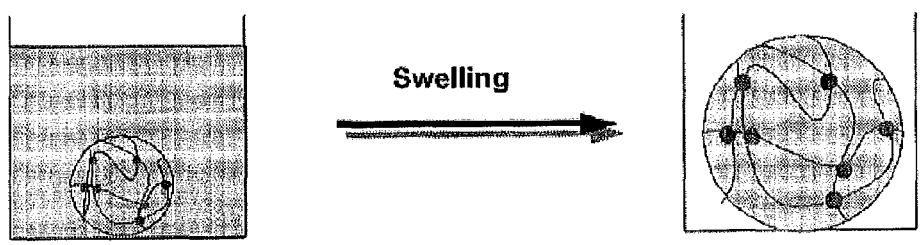
FIG. 7 schematically depicts swelling of a super-absorbent polymer upon contact with water.

In the dry state the matrix network of the super-absorbent material is folded/compressed on itself. The matrix is highly hydrophilic and expands upon hydration when it comes into contact with water (FIG. 7). The initial dry (powder or particulate) material turns into a gel, expanding to a volume several hundred times larger than the initial volume. A large percent of synthetic SAPs are powders/particles. Typical average particle size of commercially available product is about 450 µm, with a relatively narrow distribution of particle sizes.

Figure 8:
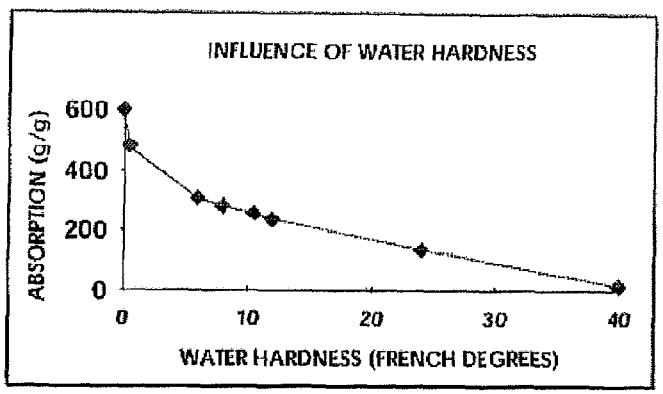
FIG. 8 shows the influence of ions and the pH on the absorption properties of super-absorbent polymers.
Figure 8:
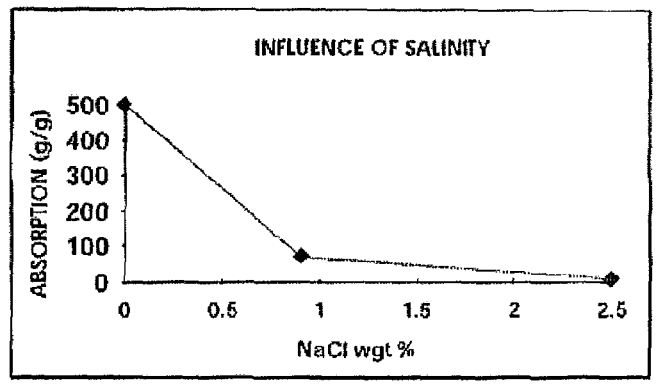
Figure 8:
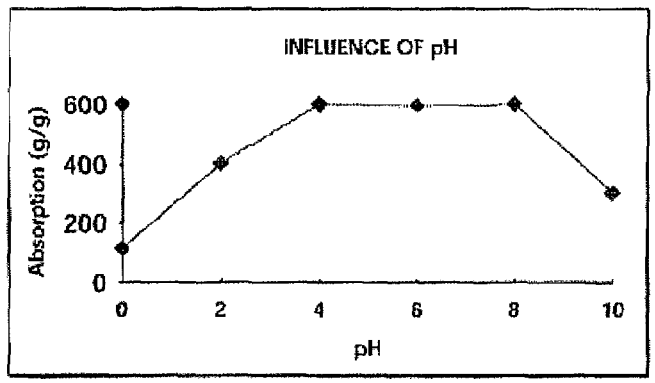

The performance of SAPs is characterized by its physical parameters: cross-linking, particle size distribution, morphology, etc., and also by the fluid they are hydrated with and/or subsequently come into contact with. The influence of ions and the pH on the absorption properties is exemplarily shown in FIG. 8. Divalent ions in hard water, such as magnesium and calcium, as well as sodium ions may significantly decrease the absorption properties of SAPs. In addition, the pH also may influence absorption with a common absorption maximum being between pH values of 4 and 8.

Figure 9:
FIG. 9 shows a picture of SAPs produced by a polymerization (gel) process, in which the monomers are polymerized in solution. SAPs resulting from this process have an irregular (chip-like) morphology.

Most SAPs are synthesized by a polymerization (gel) process, in which the monomers are polymerized in solution. This results in the formation of a polymer block, which is sieved to obtain the desired particle size. SAPs resulting from this process have an irregular (chip-like) morphology (FIG. 9).

Figure 10:
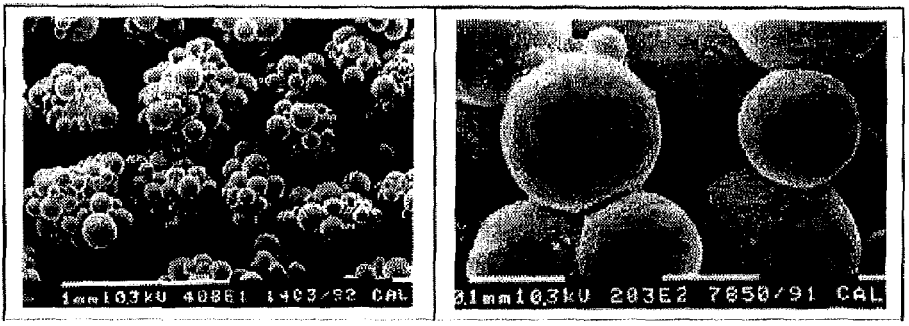
FIG. 10 shows pictures of SAPs produced using an inverse suspension process, in which monomer droplets are suspended in a media stabilized by a surfactant. This process can lead to two different morphologies.
Figure 10:
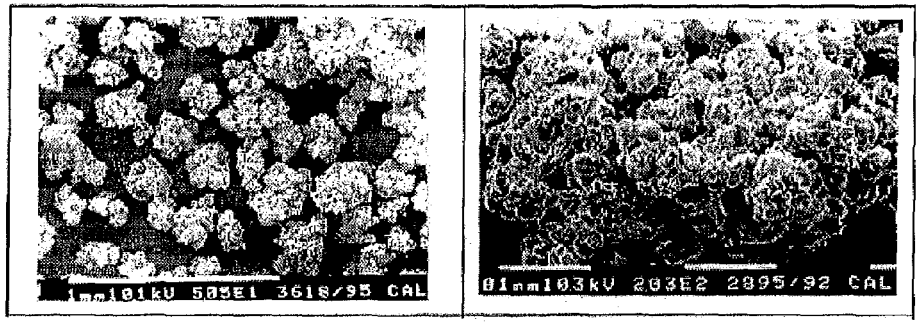

However, it is possible to obtain SAPs having a more uniform morphology. This is accomplished using an inverse suspension process, in which monomer droplets are suspended in a media stabilized by a surfactant. Polymerization takes place in each droplet, and can lead to two different morphologies, agglomerated beads (FIG. 10A) or a broccoli-like morphology (FIG. 10B). The former hydrate, when contacted with water, to produce a gel in about 100 seconds. The latter can hydrate to produce a gel in about 5 seconds due to their very high specific surface area (in the order of 1 $m^2/gm$).

Table I shows desirable characteristics of SAPs for practice in the present invention.

TABLE I

| Adsorption in demin water | About 500 g/g | | |
|---|---|---|---|
| Appearance | White powder | | |
| Available morphology | (See FIG. 10A) | (See FIG. 10B) | |
| Gelling time | 100 s | 5 s | |
| Particle size distribution | 100-800 µm | 100-500 µm | 0-150 µm |
| Bulk density | 0.74 | 0.42 | 0.60 |
| Typical products | D60 | S35 | XFS |

As further examples, the following SAPs are can be practiced in the present invention: Aquakeep® and Norsocryl® which are SAPs that are able to absorb more than several hundred times their weight of pure water in a few seconds. (Arkema, Colombes Cedex, France: www.arkema.com). After swelling, the SAP liquid becomes a gel. Generally, SAPS are practicable for the absorption and retention of non viscous fluids, and used in such disposable products such as baby diapers, training pants, adult incontinence products and sanitary napkins. These SAPs typically are cross-linked copolymers of acrylic acid and sodium acrylate.

When hydrated with NaCl 0.9% or demineralised/sterile water in a proportion not exceeding about 20% of the total absorption capacity of the above SAPs (free absorption g/g—Edana recommended test method), the heat sink can be appropriately cooled or frozen. Chilling of the hydrated superabsorbent hydrogel prior to application of the present dressing to a wound site provides the heat sink (heat absorbing) feature of the dressing.

Referring now to the drawings, the details of preferred embodiments of the present invention are graphically and schematically illustrated. Like elements in the drawings are represented by like numbers, and any similar elements are represented by like numbers with a different lower case letter suffix.

Figure 1:
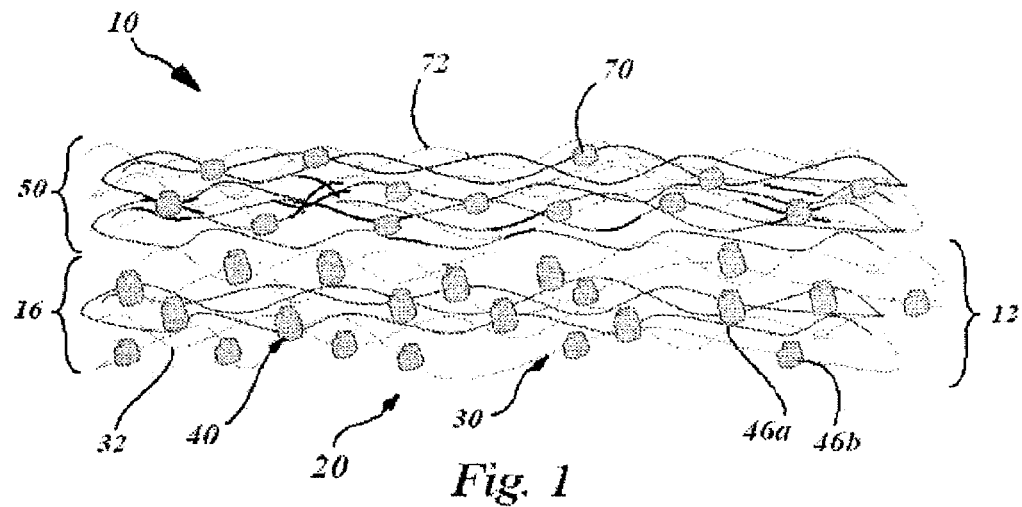
FIG. 1 is a schematic side view of a basic embodiment of the present cold adaptable wound dressing device showing a heat-sink layer adjacent a wound contacting layer.

As illustrated in FIG. 1, the present cold adapted wound dressing device 10 designed to promote healing of a wound to which it is applied comprises two main structural components: a wound covering 12; and a heat sink or heat absorbing layer 50. Additionally, the present wound dressing device 10 includes a wound treatment material 40 disposed in the wound covering 12. In a preferred embodiment exemplified in FIG. 1, the wound covering 12 has a wound contacting layer 16 with a wound contacting surface 20. A wound treatment material 40 is contained in the wound contacting layer 16. The heat absorbing layer 50 is in heat flow communication with the wound contacting layer 16. The heat absorbing layer 50 is adapted to remove heat from the wound contacting layer 16, and thus reduce the temperature of the wound contacting surface 20 to below ambient temperature. Heat from the wound area where the dressing is applied is drawn to the heat sink layer 50, which reduces the local body temperature in the area of the wound. In this manner, the present cold adapted wound dressing device 10 provides the healing benefits associated with cooling the wound site. Additionally, the wound treatment material 40 in the wound contacting layer 16 can diffuse out of the contacting layer 16 and into the wound site, and function as a bio-acting composition to biochemically promote wound healing. Therefore, the present cold adapted wound dressing device 10 provides the benefit of a duplex wound healing mechanism to actively promote healing, rather than only the passive protective function of a plain dressing. These benefits for promoting healing of the wound are: the physical function of removing heat, absorbing wound exudate and blood and the biochemical function of providing a bio-active composition The wound covering portion 12 of the present cold adapted wound dressing device 10 has a wound contacting layer 16 configured as a porous matrix 30 that allows aqueous fluids to freely diffuse into and through the matrix 30. The matrix 30 in this embodiment is comprised of a fibrous material 32. However, materials other than fibrous may be used if they are adapted to maintain the structural integrity appropriate for a wound dressing. The porous matrix 30 has fluid absorbing properties and can absorb body-fluids and/or wound exudate. Fibrous SAPs having appropriate fluid absorption properties are known in the art and are selectable by the ordinary skilled artisan for practice in the present invention. Examples of cross-linked SAP's supports practicable in the matrix are: cellulose, wood pulp, alginates, etc. The wound-contacting layer and the dressing cover top layer can comprise polypropylene, polyethylene, polyester or any other bio-compatible synthetic layer as are known in the art.

Figure 2:
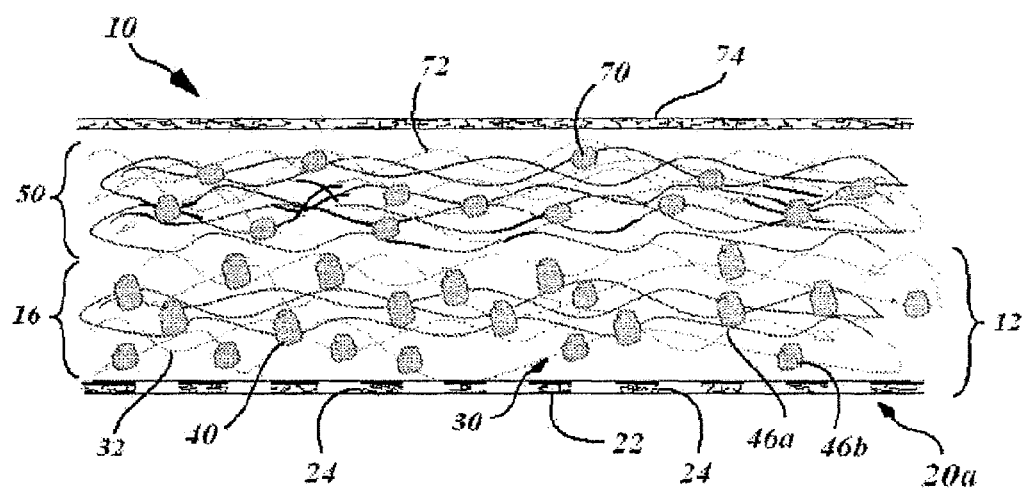
FIG. 2 is a schematic side view of an embodiment of the present cold adaptable wound dressing device showing the heat-sink layer and adjacent wound contacting layer enclosed/sandwiched between a wound contacting bottom surface layer and a dressing cover top layer.

The wound contacting layer 16 of the wound covering 12 has a wound contacting surface 20, which is intended to contact the wound at the wound site. In the embodiment exemplified in FIG. 1, is merely a surface of the wound contacting layer 16 itself. However, as exemplified in FIG. 2, the wound contacting surface 20a can be a separate porous surface layer 22 made of the same material or a material different from the wound contacting layer 16, which has an appropriate plurality of pores 24 distributed across the porous surface layer 22 to allow fluids and solutes passage through. For example, if the matrix material 30 of the wound contacting layer 16 is to be prevented from adhering to the wound, the wound contacting surface 20a can be accomplished using a non-sticking separate porous surface 22. This non-sticking separate porous surface may be impregnated with natural Hyaluronic Acid (HA) or crosslinked HA (as fibers, granules, powder, gel) or HA-compositions like creams, gels, aequeous solutions and/or chitosan, diacerhein and/or derivatives thereof. The above mentioned compositions provide anti-inflammatory functions (e.g. Diacerhein, HA) and analogues for the substitution of endogenous HA which is normally required in the wound healing process.

In another embodiment, the material of the wound contacting layer can be collagen, poly(L-lactide) (polylactic acid;

PLLA), and/or poly(glycolic-co-lactic acid) (PGLA) which are impregnated with the above mentioned compositions.

As also illustrated in the figures, the present cold adapted wound dressing device 10 has a wound contacting layer 16 that is a porous matrix 30 comprised of a fibrous material 32, which fibrous material 32 is impregnated with a wound treatment material 40. The wound treatment material 40 is a bio-affecting composition having wound healing efficacy, and can be composed of one or more active constituents 46. In the embodiment illustrated, a natural Hyaluronic Acid composition 46a is an active constituent of the wound treatment material 40. The natural Hyaluronic Acid composition can be contained in the matrix material 30 in the form of a gel, a cream, natural Hyaluronic Acid fibers 46a or a combination of any of these. Other active constituents 46b can be contained in the matrix material 30 as well, such as those noted above.

Figure 3A:
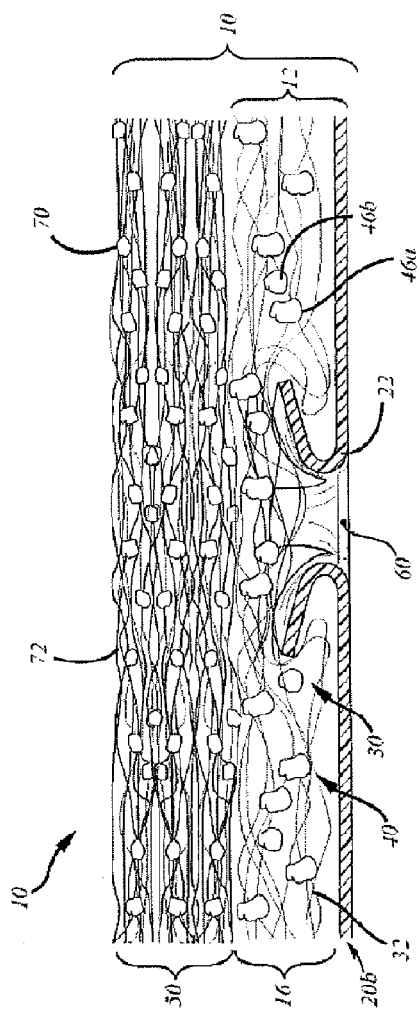
FIGS. 3A to 3D are schematic side views of alternative embodiments of the present cold adaptable wound dressing device.
Figure 3B:
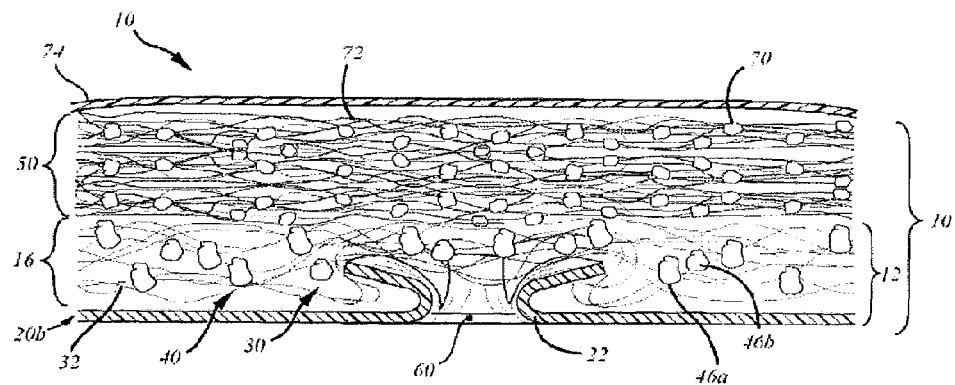
Figure 3C:
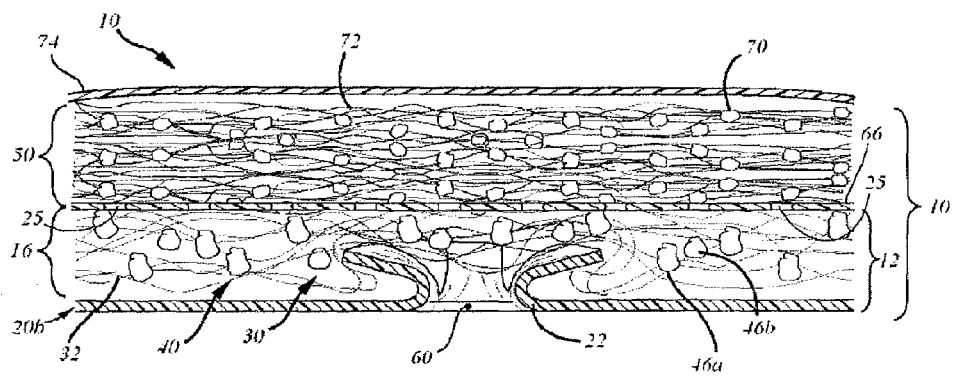
Figure 3D:
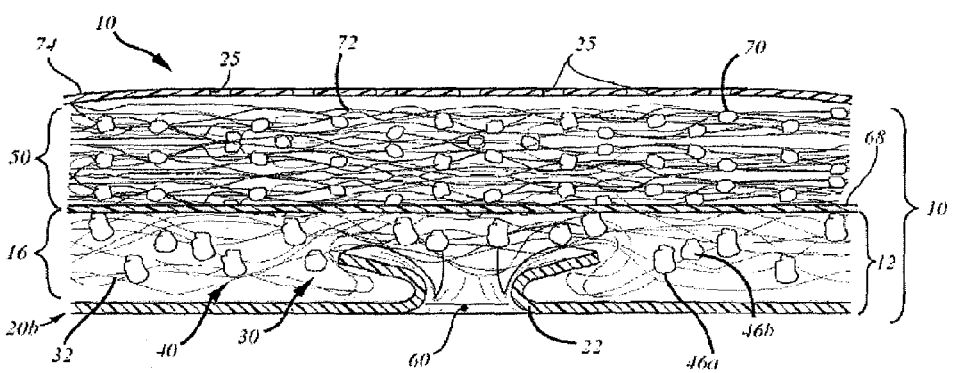

As illustrated in FIG. 3A, the present cold adapted wound dressing device 10 wherein the wound covering 12 has a wound contacting surface 22a that is a separate porous surface of the wound contacting layer 16, the separate porous surface 22a having physical surface features 60 that mechanically engage the wound contacting layer 16. The physical surface feature 60 serves to engage the wound contacting layer 16 and prevent it sliding relative to the wound contacting surface 22a, and to prevent the disengagement of the wound contacting layer 16 from the wound contacting surface 22. This is useful in view of the hydrated nature of the heat absorbing layer 50 in embodiments where the heat absorbing layer 50 is in fluid communication with the wound contacting layer 16. For example, in FIGS. 3A and 3B, the heat absorbing layer 50 is in open fluid flow communication with the wound contacting layer 16. In FIG. 3C, a partial fluid barrier 66 separates the heat absorbing layer 50 from the wound contacting layer 16. In this embodiment, the heat absorbing layer 50 is in partially restricted fluid flow communication with the wound contacting layer 16, because of the pores 25 through the partial fluid barrier 66. In FIG. 3D, a full fluid barrier 68 separates the heat absorbing layer 50 from the wound contacting layer 16. The full fluid barrier 68 may allow gas exchange through the layers. In this embodiment, the heat absorbing layer 50 precluded from being in fluid flow communication with the wound contacting layer 16. In the embodiments illustrated in FIGS. 3A to 3D, the engaging surface features 60 are holes roughly punched through the separate wound contacting surface 22a. The physical surface features are not necessarily the same as the pore feature 24 of the separate porous layer 22. Although a physical surface feature 60 may additionally serve the passage function of a pore feature 24, they also provide a mechanical engagement feature that a simple pore feature 24 may not.

In the preferred embodiment illustrated, the heat absorbing layer 50 of the cold adapted wound dressing device 10 comprised a hydrated "super absorbent polymer" (SAP) 70. SAPs 70 are known in the field. Examples include those disclosed in U.S. Pat. No. 5,750,585 to Parl et al. and U.S. Pat. No. 6,800,278 to Perrault et al. Choice of the SAP 70 to be practiced and it relative bio-compatibility will influence whether an embodiment wherein the heat absorbing layer 50 is in flow communication with the wound contacting layer 16 can be practiced.

To make the present cold adapted wound dressing device 10 a self contained unit, a bandage covering 74 can be added to the top surface 72 of the heat sink layer 50. See FIGS. 3B to 3D. The bandage covering 74 can be accomplished using any of a number of materials and configurations known to and selectable by one of skill in the art. For example, the top covering dressing layer 74 can be occlusive, can have limited gas-permeability or can it have pores 25 to pass fluids. The top covering dressing layer 74 can protected with an adhesive backed covering (not shown).

Figure 4:
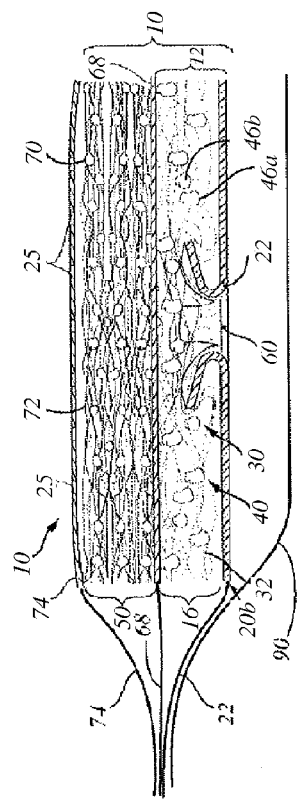
FIG. 4 is a side cross-sectional view of the embodiment of FIG. 3D showing the extension of certain support layers to form a "piggy-back" configuration, wherein the SAP matrix can be separately hydrated, while the wound contacting matrix is maintained in a sterile condition by a separate, removable sterile cover.

Also, as exemplified in FIG. 4, the embodiment of FIG. 3D can be adapted to form a "piggy-back" configuration, wherein the SAP matrix 50 can be separately hydrated, while the wound contacting matrix 12 is maintained in a sterile condition by a separate, removable sterile cover 90.

The inventive wound dressings can be used in methods for promoting the healing of a wound in a patient, for example a mammal, such as a human being, said methods comprising applying the wound dressings of the invention to said wound.

The invention is further illustrated by the following non limiting examples and the appended figures. As one of ordinary skill in the art will readily appreciate from the disclosure of the present invention, other compositions of matter, means, uses, methods, or steps, presently existing or later to be developed that perform substantially the same function or achieve substantially the same result as the corresponding exemplary embodiments described herein may likewise be utilized according to the present invention.

EXAMPLES

Example 1

Loading the Matrix with Hyaluronic Acid

Adequate amounts of matrix material, like cellulose fibers, thermoplastic fibers and SAP powder with a total weight of 50-500 g/m$^2$ were given into a powder mixer along with a defined quantity of dry medical grade sodium hyaluronate granules (for example a quantity to obtain a HA concentration of 0.1% w/w) and mixed for one hour at 120 rpm. Thereafter the resulting mixture was compressed by a calendar press at 55° C. to a dry "cake" with a diameter of 2-4 mm. A matrix obtained by this process, when being eluted with water having a temperature of 36° C., will release 60-80% of the HA as determined by the carbazol method. This shows that a matrix loaded with HA can serve as a reservoir for the uptake and release of HA to wound surfaces.

Example 2

Loading the Matrix with Deacetylated Chitosan

The same process was used for loading the matrix with medical grade chitosan of animal or non-animal origin, which is characterized by a deacetylation ratio of 60-95%.

Example 3

Impregnating the Encasing Material with Hyaluronic Acid

Webs of non-woven thermoplastic fibers of an adequate texture and strength were lead through an aerosol chamber first and, subsequently, through a drying chamber in order to achieve an impregnation of the encasing material with 0.1 to 0.5% of HA (w/w). Spraying and padding the nonwoven material with HA based aqueous solutions before drying are alternative methods of impregnation.

Example 4

Bonding the Matrix with the Encasing Material

Mechanical stabilization of the matrix inside the encasing material is an important measure in order to avoid lumping/ agglomeration leading to dislocation of the matrix material inside the pad once this is soaked with water and exposed to vertical forces. This was achieved, for example, by partial ultrasound bonding of the encasing material to the matrix, which—to this extent—contained an adequate amount of thermoplastic fibers or powder.

Example 5

Positive Cooling and Wound-Healing Effects of the Device

A sterilized prototype version of the cold-adapted wound dressing device was used in patients after arthroscopic meniscectomy in order to improve their postsurgical course. The pads were sterilised by ethyleneoxide and unpacked in the sterile op-environment.

Thirty patients were included in this pilot, comparative study and divided into 2 groups, a prototype wound pad treatment group (n=20 patients) and a control group (n=10 patients) The prototype wound pad treatment group underwent the following procedures:

After completion of arthroscopic meniscectomy, steri-strips were used for skin closure in all the 20 patients. For each patient a prototype cold-adapted wound dressing device (size 12×22 cm) was removed from the sterile packaging and about 100 mL 0.9% NaCl (approx. 0.5-0.8 mL NaCl/cm$^2$) cooled to 4° C. were poured into the upper part of the device. The prototype cold-adapted wound dressing device retained this cold water in the SAP part of the device. 10 ml of Viscoseal (TRB Chemedica), a sterile viscoelastic solution containing 0.5% fermentative hyaluronic acid in a buffer solution, was applied to the lower part of the prototype cold-adapted wound dressing device which would be placed in contact with the wound surface. The prototype cold-adapted wound dressing device was then applied onto the closed incisions wounds (3 per joint) and was covered with an occlusive dressing and an elastic bandage. Patients were prescribed analgesics or classical NSAIDs and the number taken by each patient was recorded.

The control group underwent the following procedures: After completion of arthroscopic meniscectomy, Steri-strips were used for skin closure in the 10 patients in this group. Standard, commercially available wound dressings were placed on the wound. No cooling packs were used in this group of patients. Patients were prescribed classical NSAIDs and the number taken by each patient was recorded. Analgesics were prescribed in case patients still had pain despite the intake of NSAIDs and the type and amount of analgesics taken by each patient was recorded Pain in the treated joint was assessed by the patient at about 1 hour post-surgery (by which time the anaesthetic had worn out), and then every 2 hours over a 24 hour post-operative period (when the patient was awake), using a 100 mm visual analogue scale (VAS). This scale has a zero (0) anchor point indicating "no pain" and one hundred anchor point (100) indicating "intense pain".

Skin temperature was measured by a nurse every 10 minutes for the 1$^{st}$ hour after surgery using a standard thermometer, the tip of which was placed adjacent to the skin in the operated region).

Determined or monitored were:
 the duration of skin temperature reduction;
 analgesic consumption in addition to regular NSAIDS intake;
 joint effusion;
 skin maceration; and
 tolerance to cryotherapy or allergic reactions to HA/adverse events Results showed that, in the prototype cold-adapted wound dressing device group, the mean value for pain was 3 cm on the VAS (range: 2-6 cm) in the first 24 hours and 2 patients required a single dose of an analgesic in addition to their NSAIDs at the time of discharge from the hospital about 24 hours post-surgery.

In the control group, the mean value for pain was 4.5 cm (range 2-9 cm) in the first 24 hours and 5 patients required analgesics in addition to their NSAIDs at the time of discharge from the hospital about 24 hours post-surgery.

It can be concluded that, in comparison to standard dressing, the prototype cold-adapted wound dressing device rapidly decreased post-operative pain and surprisingly had an NSAID-sparing effect. The most significant pain reduction was in the first 4 hours post-surgery in comparison to the control group and patients required fewer escape medication post surgery.

The skin temperature near the operation site was taken immediately after the completion of arthroscopy and application of Steri-strips (baseline values) and every 10 minutes thereafter for the first 60 minutes after surgery in both groups. The mean temperature of the skin near the operation site in both groups of patients was 33° C.

In the prototype cold-adapted wound dressing device group, the mean skin temperature decreased to 14° C. at 5 minutes after application of prototype device and remained at a low level for a mean period of 22 minutes. Thereafter there was a progressive increase in skin temperature over the next 33 minutes to reach 30° C.

Skin temperature in the control group remained at a mean value of 32° C. for the first 60 minutes.

In conclusion, the prototype cold-adapted wound dressing device caused a significant decrease in skin temperature compared to the control group.

Surprisingly, the use of the cooling pad did not result in condensation of humidity on the skin and no skin maceration was observed in the prototype wound pad-treated group during the observation period of 24 hours.

The prototype wound pad was stained with wound exudate but remained dry after absorbing the exudate. The wound contacting surface of the prototype stayed dry due to the residual humidity absorbing capacity of the SAP layer.

Patients in the prototype wound pad-treated group had more rapid primary wound healing in all 60 incisions (3 per knee) with no infections observed. At the 6 month visit, no cheloid formation or delayed wound healing was observed.

In the control group, primary wound healing in all 30 incisions (3 per knee) was slower with more exudate formation but no infections were observed. At 6 months, 2 patients showed cheloids.

In conclusion, the above results showed that the prototype wound pad was safe and effective in post-operative wound care. By its skin cooling effect it reduced the amount of wound exudates and hematoma compared to the control group. The more rapid wound repair in the prototype wound pad-treated group was probably due to the presence of hyaluronic acid. The wound surface was slightly moist and no skin maceration or other adverse event was observe While the above description contains many specifics, these should not be construed as limitations on the scope of the invention, but rather as exemplifications of one or another preferred embodiment thereof. Many other variations are possible, which would be obvious to one skilled in the art.

Accordingly, the scope of the invention should be determined by the scope of the appended claims and their equivalents, and not just by the embodiments.

All documents cited herein are incorporated by reference in their entirety.

What is claimed is:

1. A cold adapted wound dressing device (10) designed to promote healing of a wound to which it is applied, the dressing device (10) consisting essentially of:
    a wound covering (12) having a wound contacting layer (16) with a wound contacting surface (20);
    a wound treatment material (40), wherein the wound contacting layer (16) consists essentially of the wound treatment material (40); and
    a heat absorbing layer (50) in heat flow communication with the wound contacting layer (16), the heat absorbing layer (50) adaptable to remove heat from the wound contacting layer (16) and reducing a temperature of the wound contacting surface (20) to below an ambient temperature, to provide the cold adapted wound dressing device (10) for promoting healing of the wound,
    wherein the wound contacting layer (16) is a porous matrix (30) that allows aqueous fluids to freely diffuse into and through the matrix, the matrix comprising a fibrous material (32) which is impregnated with the wound treatment material (40), wherein the wound treatment material (40) consists essentially of a natural Hyaluronic Acid and/or Chitosan and/or Diacerhein, and wherein the heat absorbing layer (50) comprises a hydrated super absorbent polymer (70) that is hydrated to not more than 20 percent of the polymer's capacity.

2. The cold adapted wound dressing device (10) of claim 1, wherein the wound contacting layer (16) has fluid absorbing properties and can absorb body-fluids or wound exudate.

3. The cold adapted wound dressing device (10) of claim 1, wherein the wound contacting surface (20) is a surface of the wound contacting layer (16).

4. The cold adapted wound dressing device (10) of claim 1, wherein the wound covering (12) has a wound contacting surface (20) that is a separate porous surface of the wound contacting layer (16).

5. The cold adapted wound dressing device (10) of claim 1, wherein the wound covering (12) has a wound contacting surface (20) that is a separate porous surface of the wound contacting layer (16), the separate porous surface (20) having physical surface features (60) that engage the wound contacting layer and serve to prevent sliding of the wound contacting layer (16) relative to the wound contacting surface (20) and the disengagement of the wound contacting layer (16) from the wound contacting surface (20).

6. The cold adapted wound dressing device (10) of claim 1 wherein the wound treatment material (40) consists essentially of a natural Hyaluronic Acid composition in a form selected from the group consisting of: a gel, a cream and an aqueous solution of natural Hyaluronic acid.

7. The cold adapted wound dressing device (10) of claim 1, wherein the heat absorbing layer (50) is in open fluid flow communication with the wound contacting layer (16).

8. The cold adapted wound dressing device (10) of claim 1, further comprising a partial fluid barrier (66) separating the heat absorbing layer (50) from the wound contacting layer (16), wherein the heat absorbing layer (50) is in partially restricted fluid flow communication with the wound contacting layer (16).

9. The cold adapted wound dressing device (10) of claim 1, further comprising a fluid barrier (68) separating the heat absorbing layer (50) from the wound contacting layer (16), said fluid barrier (68) allowing gas exchange through the heat absorbing layer (50) and the wound contacting layer (16).

10. A method for promoting healing of a wound in a subject in need thereof, comprising applying the cold adapted wound dressing device of claim 1 to said wound.

\* \* \* \* \*